United States Patent
Lipson et al.

(10) Patent No.: US 6,970,249 B1
(45) Date of Patent: Nov. 29, 2005

(54) PLASMON RESONANCE PHASE IMAGING

(75) Inventors: Stephen Lipson, Haifa (IL); Ariel Notcovich, Haifa (IL)

(73) Assignee: Proteoptics, Ltd., Haifa (IL)

( * ) Notice: Subject to any disclaimer, the term of this patent is extended or adjusted under 35 U.S.C. 154(b) by 94 days.

(21) Appl. No.: 10/088,654

(22) PCT Filed: Sep. 12, 2000

(86) PCT No.: PCT/IL00/00559

§ 371 (c)(1),
(2), (4) Date: Mar. 14, 2002

(87) PCT Pub. No.: WO01/20295

PCT Pub. Date: Mar. 22, 2001

(30) Foreign Application Priority Data

Sep. 15, 1999 (IL) ........................................ 131903

(51) Int. Cl.⁷ .......................... G01N 21/55; G01B 9/02
(52) U.S. Cl. ...................................... 356/445; 356/517
(58) Field of Search .............................. 356/450, 454, 356/517, 505, 506, 445

(56) References Cited

U.S. PATENT DOCUMENTS

| | | | | |
|---|---|---|---|---|
| 5,185,810 A | * | 2/1993 | Freischlad | 382/100 |
| 5,220,403 A | * | 6/1993 | Batchelder et al. | 356/450 |
| 5,415,842 A | * | 5/1995 | Maule | 422/82.05 |
| 5,999,262 A | * | 12/1999 | Dobschal et al. | 356/456 |
| 6,628,376 B1 | * | 9/2003 | Nikitin et al. | 356/38 |

* cited by examiner

Primary Examiner—Andrew H. Lee
(74) Attorney, Agent, or Firm—William H. Dippert; Wolf, Block, Schorr and Solis-Cohen LLP (57) ABSTRACT

A device for measuring simultaneously the phase at each point of an image formed by light reflected from a sample in which the phase has been modified by plasma resonance in a thin conducting layer, the device comprising a thick transparent substrate (10) on which a thin layer of conducting material is deposited (13); a light source (1); an interferometer; an imaging means (9); and a processing means.

2 Claims, 6 Drawing Sheets

PLASMON RESONANCE PHASE IMAGING

FIELD OF THE INVENTION

The present invention relates to the detection and measurement of very small changes in a field expressed by changes in the refractive index close to a given surface. More particularly it relates to a device and method for plasmon resonance phase imaging.

BACKGROUND OF THE INVENTION

The refractive index of a medium is commonly measured by observing the phase change of an electromagnetic wave traversing a given distance within the medium.

Methods of measuring the refractive index field of a non-uniform specimen are well known. These methods rely on the transmission of a light wave through the medium in question. After it has traversed the medium, a light wave interferes with a reference wave which has not traversed the medium and the interference pattern so obtained is analyzed by means of a computer to give the refractive index in each pixel of the field. The refractive index has been interpreted in various ways, to indicate temperature or solute concentration, for example. The resolution of the methods used to date are limited by the accuracy to which the optical phase change can be determined at each point in the field. This limit is typically $2\pi/100$ for a single pixel, and may be $2\pi/1000$ for a complete field.

U.S. Pat. No. 5,120,131 (Lukosz), titled METHOD AND APPARATUS FOR SELECTING DETECTION OF CHANGES IN SAMPLES BY INTEGRATED OPTICAL INTERFERENCE, filed Aug. 10, 1990, is an example for such method. In an integrated optical interference method, polarized laser light is coupled into a planar waveguide, propagates in the waveguide as a guided wave, which consists of two mutually coherent, orthogonally polarized modes, interacts at least once with the sample, which is applied to the surface of a section of the waveguide called measuring section, and subsequently is coupled out of the waveguide. The time dependent phase difference between the two orthogonal polarization components of the out-coupled light is measured with a device comprising photodetectors and polarization optical components.

In U.S. Pat. No. 5,804,453 (Chen), filed Feb. 9, 1996, titled FIBER OPTIC DIRECT-SENSING BIOPROBE USING A PHASE TRACKING APPROACH there was disclosed a method of determining the concentration of a substance in a sample solution using a fiber optic probe having a reagent at its distal end to which the substance bonds. It comprises a fiber optic bioprobe in which an immobilized biolayer, such as an antigen or antibody, acts as a sensing etalon of a Fabry-Perot interferometer. The bioprobe is used in a system in which a shift in the spectral dispersion pattern, caused by reflected out-of-phase beams, is used to determine a concentration of a substance in a sample solution. The method disclosed in this patent investigates the phase difference in the sample caused by the presence of the substance in the sample solution, by examining the interference patterns of the sample. The method does not include the employment of surface plasmon resonance, nor does it provide an image of the sample.

In U.S. Pat. No. 5,442,448 (Knoll), filed Mar. 21, 1994, titled DEVICE FOR THE LATERALLY RESOLVED INVESTIGATION OF A LATERALLY HETEROGENEOUS ULTRATHIN OBJECT LAYER, there was disclosed a device for the investigation of a laterally heterogeneous ultrathin object layer, especially for the laterally resolved detection of a change in the layer thickness of the object layer which results from a specific binding reaction of a first binding partner bound to the object layer with an unbound second binding partner. The device has a multi-layer structure which extends into the investigation region and includes the object layer as first layer and a second layer adjacent to the latter, a coupler arrangement for the coupling of excitation light into the second layer. The excitation light generates at least one defined angle of incidence in the second layer a bound, non-radiating electromagnetic wave, from which an evanescent wave extends into the object layer. An optical imaging system is provided for the imaging of the investigation region of the object layer in an image plane at a defined angle of emergence, at which detection light is coupled out from the second layer. The coupler arrangement includes an optical grating structure which extends into the investigation region parallel to the object layer and which is rotatable about an axis extending perpendicular to the grating plane. This allows adjustment of the image contrast, by varying the orientation of the grating lines relative to the plane of incidence. In contrast to U.S. Pat. No. 5,804,453 (Chen) this invention does employ surface plasmon resonance on metal, and does provide an image, but it is not concerned with the phase change on reflection from the sample, nor does it employ interference.

In U.S. Pat. No. 5,313,264 (Ivarsson et al.), filed May 10, 1991, titled OPTICAL BIOSENSOR SYSTEM, there was disclosed an optical biosensor system using internal reflection versus angle of incidence determination for the detection of biomolecules, the system comprising a sensor unit with at least two sensing surfaces, a source of light, and means for forming a convergent beam of light which is focused in a wedge-shape fashion to form a streak of light extending transversely over all the sensing surfaces; a photodetector device; in the form of a two-dimensional matrix of individual photodetector; optical imaging instrumentation in the form of an anamorphic lens system for the purpose of imaging rays of reflected light from the sensing surfaces on each its own column of photodetectors, so that for each sensing surface there is a corresponding set of columns of photodetectors; and an evaluation unit for determining the minimum reflectance or the resonance angle at each of the sensing surfaces. The invention also relates to a method for calibrating the biosensor system, a method for correcting for baseline drift as well as a method for temperature regulation of thermostat means in the biosensor system. This system employs surface plasmon resonance, but does not investigates the phase nor does it provide an image, and is merely concerned with local sensing.

In U.S. Pat. No. 5,237,392 (Hickel et al.), filed Aug. 13, 1992, titled DETERMINATION OF REFRACTIVE INDEX AND THICKNESS OF THIN LAYERS, the refractive index and thickness of ultrathin layers less than 1 micrometer in thickness are determined by recording the layers, which have been applied to a solid support, by surface plasmon microscopy as a function of the angle of incidence of the incident laser beam, the method making it possible to determine layer thicknesses with a vertical resolution greater than or equal to 0.1 nm and a simultaneous lateral resolution greater than or equal to 5 $\mu$m. This invention deals with surface plasmon resonance and produces an image, but does not examine the phase change of the reflected or transmitted light.

Plasma resonance in a metal film has been used to increase the contrast of images of objects characterized by very small variations of optical refractive index (see Hickel W., Rothenhauser B., and Knoll W., *Surface plasmon microscopic characterization of external surfaces*, J. App. Phys. 66(1989) 4832–4836, Rothenhauser B., and Knoll W., *Surface-plasmon microscopy*, Nature 332 (1988) 615, and Yeatman E. and Ash E. A., *Surface-plasmon microscopy*, Elec. Lett 23 (1987) 1091).

It is a purpose of the present invention to provide a method of displaying the refractive index of each pixel of the image of a sample, using an accurate method of measuring the optical phase change at each point In the field of view, similarly to the method described Kostianovsky et al. (Kostianovsky S., Lipson S. G., and Ribak E., Appl. Optics 32 (1993) 4744, and see also Raz E. et al., Phys. Rev. A 40 (1989) 1089). In addition, it is a purpose of this invention to provide an experimental method and apparatus to carry out such a measurement and provide the said display of the refractive index field in the form of an image.

BRIEF DESCRIPTION OF THE INVENTION

It is therefore provided, in accordance with a preferred embodiment of the present invention, a device for measuring simultaneously the phase at each point of an image formed by light reflected from a sample, in which the phase has been modified by plasma resonance in a thin conducting layer which is close to, or in contact with, the sample whose image is being recorded, the device comprising:

a thick transparent substrate with a planar surface on which a thin layer of conducting material is deposited, onto which is placed the sample being investigated, either in contact with it or a short distance from it;

a light source linearly polarized in a predetermined direction, whose light beam is reflected from said thin layer of conducting material from the side opposite to that on which the sample is placed at an angle substantially equal to that at which the interaction with the plasma resonance is maximized, the evanescent light field on the far side of the conducting film interacting with the sample, thus modifying the reflected light;

an interferometer which enables the reflected beam to be compared interferometrically with a reference beam derived from the same source, but not having had any interaction with the sample;

imaging means for recording an image of the planar surface in interference with the reference beam, and digitizing it; and processing means for processing said digitized image to provide an output image.

Furthermore, in accordance with a preferred embodiment of the present invention, the light source is a quasi-monochromatic or polychromatic source.

Furthermore, in accordance with a preferred embodiment of the present invention, the light source is a laser.

Furthermore, in accordance with a preferred embodiment of the present invention, the laser is a He—Ne laser.

Furthermore, in accordance with a preferred embodiment of the present invention, the light source is polarized in the p-plane, relative to the sample.

Furthermore, in accordance with a preferred embodiment of the present invention, the interferometer is a Mach-Zehnder interferometer.

Furthermore, in accordance with a preferred embodiment of the present invention, the interferometer is a Linnik interferometer.

Furthermore, in accordance with a preferred embodiment of the present invention, the light beam is illuminated annularly, with appropriate radial polarization, so as to Illuminate the sample isotropically at an angle substantially equal to that at which the interaction with the plasma resonance is maximized.

Furthermore, in accordance with a preferred embodiment of the present invention, the imaging means is a Charge-Coupled-Device camera.

Furthermore, in accordance with a preferred embodiment of the present invention, the image is recorded on a permanent recording material such as photographic film.

Furthermore, in accordance with a preferred embodiment of the present invention, the camera is connected to a computer or other processing device which digitized its output signal and calculates the phase of the reflected image in each pixel using known algorithms.

Finally, there is provided, in accordance with a preferred embodiment of the present invention, a method of measuring simultaneously the phase at each point of an image formed by light reflected from a sample, in which the phase has been modified by plasma resonance in a thin conducting layer which is close to, or in contact with, the sample whose image is being recorded, the method comprising the following steps:

One) placing the sample being investigated onto a thin layer of conducting material which is deposited on a thick transparent substrate;

Two) reflecting a light beam linearly polarized in a predetermined direction from said thin layer of conducting material from the side opposite to that on which the sample is placed, at an angle substantially equal to that at which the interaction with the plasma resonance is maximized, the evanescent light field on the far side of the thin layer of conducting material interacting with the sample, thus modifying the reflected light;

Three) interferometrically comparing said reflected beam with a reference beam derived from the same source, but not having had any interaction with the sample;

Four) recording an image of a planar surface in interference with the reference beam;

Five) digitizing said image; and

Six) processing said digitized image to obtain an output image.

BRIEF DESCRIPTION OF THE FIGURES

In order to better understand the present invention, and appreciate its practical applications, the following Figures are provided and referenced hereafter. It should be noted that the Figures are given as examples only and in no way limit the scope of the invention as defined in the appended claims. Like components are denoted by like reference numerals.

DETAILED DESCRIPTION OF THE INVENTION AND FIGURES

Figure 3:
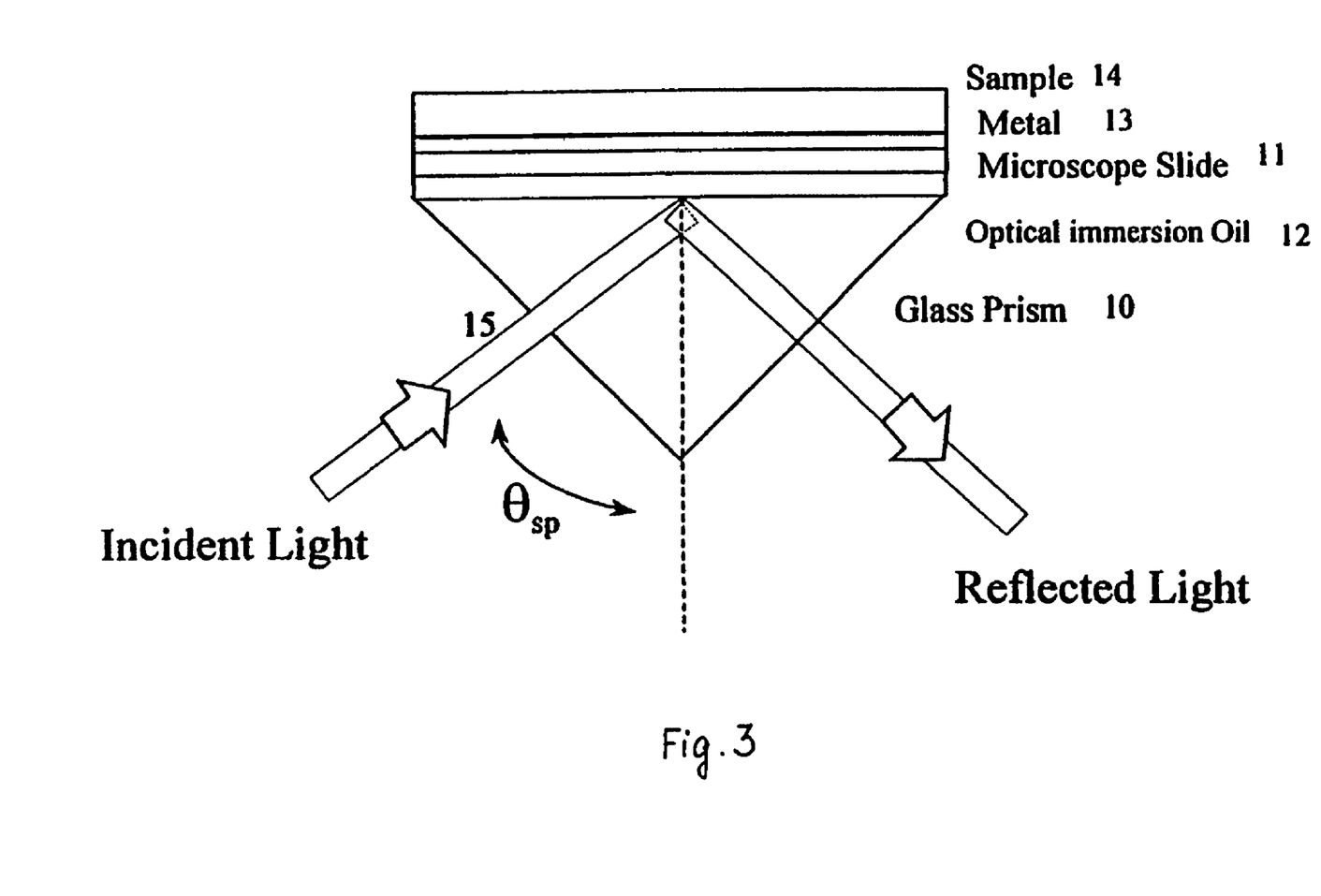
FIG. 3 shows in detail the construction of the sample and prism in the embodiment shown of FIG. 2.

As mentioned before, in the prior art, plasma resonance in a metal film has been used to increase the contrast of images of objects characterized by very small variations of optical refractive index (Yeatman and Ash, Roftenhausner and Knoll, Hickel and Knoll, Hickel Kamp and Knoll). Laser light polarized in the p-plane is incident on a sample, substantially as shown In FIG. 3, and the reflected light is imaged onto a screen or camera. The recorded image is processed so as to increase its contrast. These applications take advantage of the light absorption, which takes place preferentially under conditions of plasma resonance.

In the present invention, however, it is not the absorption but the phase change of the light which is used to create the image; the phase change is not visible directly but must be extracted from the light signal by means of a technique such as interferometry (or other phase-change measurement techniques such as wave-front curvature sensing, or phase contrast microscopy).

In the present invention the phase change is observed and measured when light is reflected from a surface in contact with the medium. The result indicates the refractive index of a thin layer of thickness of the order of one or a few wavelengths—up to about 3 wavelengths—of the radiation being used for the investigation. The method is based on the use of plasma resonance in a thin film of metal, alloy or other conductor (for example noble metals such as silver, gold) deposited onto an optical surface from which light is reflected at an angle greater than the critical angle for that component The field of refractive index which is measured in the method disclosed in this invention can be interpreted in many ways, in which a specific property, which depends on the refractive index, is assigned to each pixel of the image obtained.

In the present invention the phase change is amplified by means of excitation of plasma resonance in a conducting film in proximity to the sample under investigation. The application of plasma resonance to the measurement of refractive index is known (see above).

Electromagnetic radiation is totally reflected from a thin film of conductor, several nanometer thick, deposited on an optical surface. Despite the fact that the reflection is total, it is well known that the electromagnetic field penetrates a short distance into the medium on the other side of the reflecting surface. This penetration samples the medium to a depth of up to a few wavelengths. When the angle of reflection satisfies the resonance condition (more on that see Raether H., *Surface plasmons*, Springer-Verlag, Berlin 1988), which depends on the refractive index of the substrate and of the overlying medium, the reflected light is both absorbed and undergoes a phase change, both of which are related quantitatively to the properties of the medium within the penetrated region. If the overlying medium is not uniform in its properties, the degree of absorption and the phase of the reflection are observed to vary from point to point in the field which is illuminated. The variation of degree of absorption from point to point has been described by Rothenhauser and Knoll to image a field of refractive index or thickness in the overlying medium. However, the phase change has not been used for the purpose of imaging a whole field of refractive index or other property, since methods of measuring the phase change accurately at each point in the field are not well-known.

Figure 1:
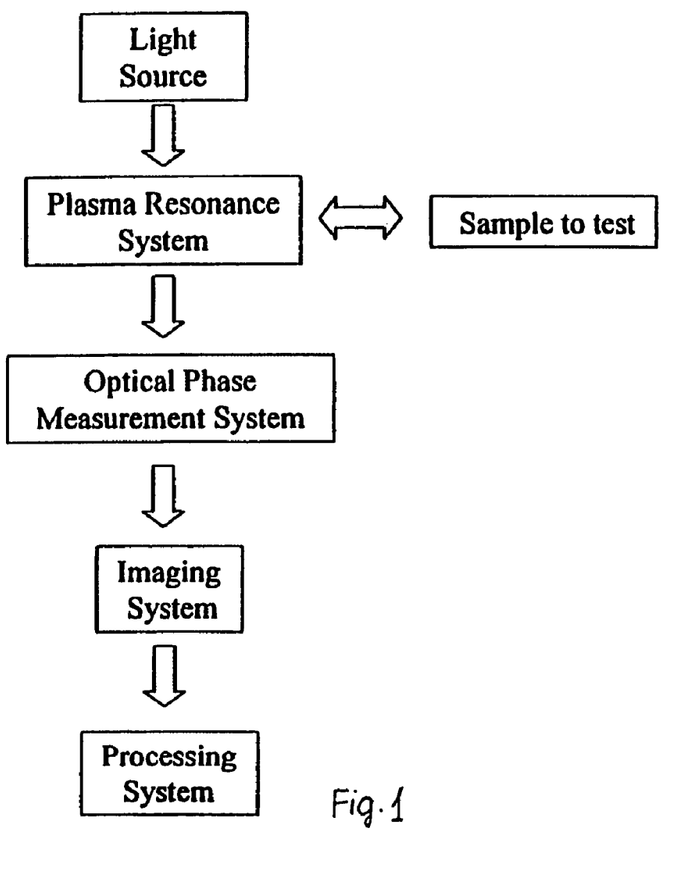
FIG. 1 illustrates a block diagram highlighting the main features of a surface plasmon resonance phase imaging device in accordance with a preferred embodiment of the present invention showing the relationship between its various parts.

FIG. 1 illustrates a block diagram highlighting the main features of a surface plasmon resonance phase imaging device in accordance with a preferred embodiment of the present invention showing the relationship between its various parts. These are discussed in details with reference to the Figures.

The basic components of the device of the present invention are:

One) a sample to be investigated which is placed onto a thin layer of a conducting material;

Two) a source of light (monochromatic light source, or a quasi-monochromatic or polychromatic source.) linearly polarized in a predetermined direction, which illuminates the sample by reflection from the thin conducting layer 13 from the side opposite to that on which the sample is placed;

Three) An optical phase measurement system which enables the reflected beam to be compared interferometrically with a reference beam derived from the same source, but not having had any interaction with the sample;

Four) an imaging system which creates an image of the planar surface in interference with the reference beam, and allows this image to be recorded;

Five) a processing system in which the recorded image is digitized and processed to provide the output display.

Figure 2:
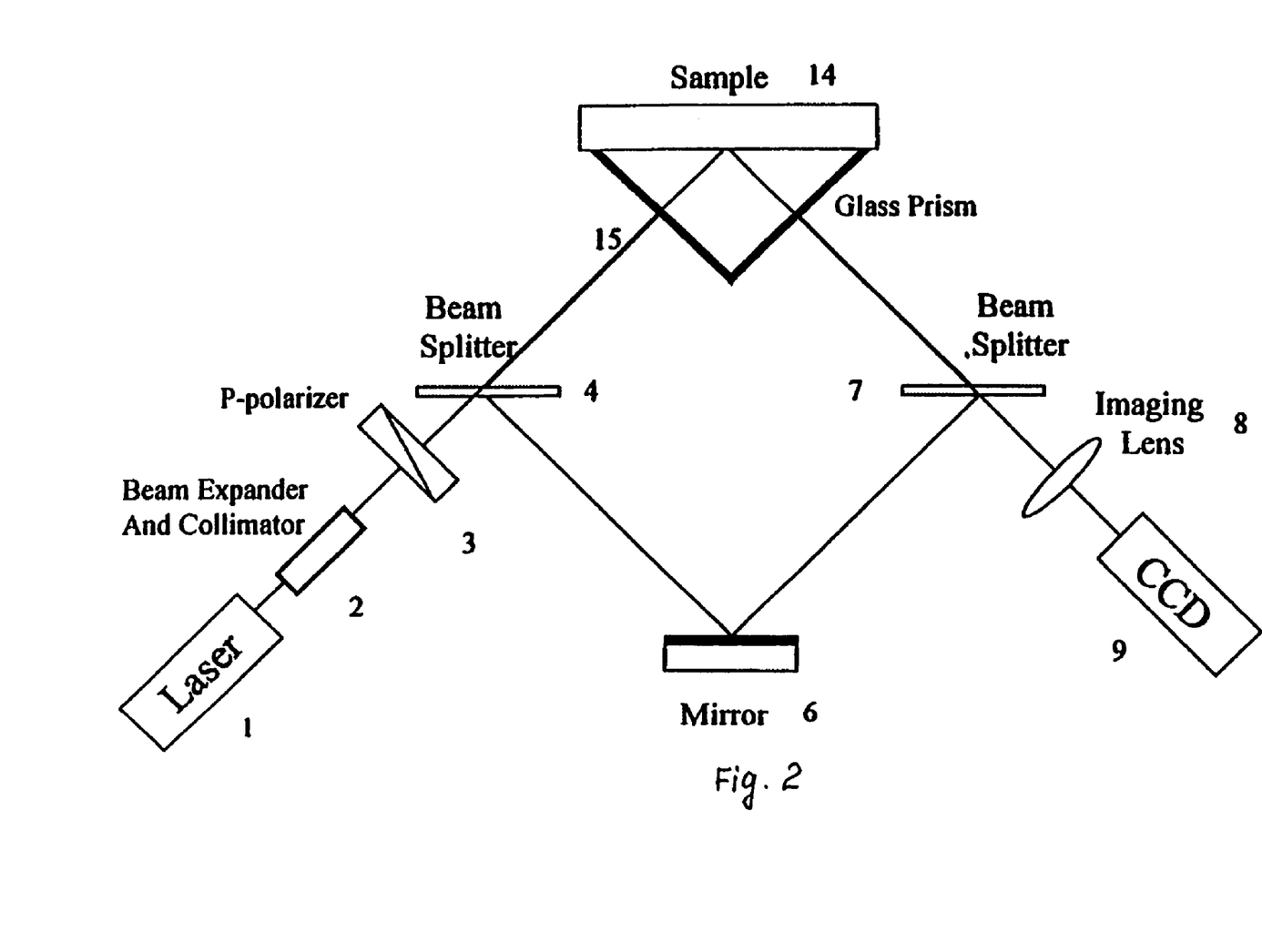
FIG. 2 depicts an overhead view of a surface plasmon resonance phase imaging device in accordance with a preferred embodiment of the present invention, in which a Mach-Zehnder interferometer is incorporated and the sample is placed on the horizontal surface of a slide cemented to the hypotenuse of a right-angled glass prism.

Reference is now made to FIGS. 2 and 3. A preferred embodiment of the present invention is illustrated schematically in FIG. 2 depicting an overhead view of a surface plasmon resonance imaging device in accordance with a preferred embodiment of the present invention, in which a Mach-Zehnder interferometer is incorporated and the sample is placed on the horizontal surface of a slide cemented to the hypotenuse of a right-angled glass prism. FIG. 3 shows in detail the construction of the sample and prism in the embodiment shown of FIG. 2.

The substrate consists of a right-angled glass prism 10. A microscope slide 11, covered with a thin film of metal 13, preferably silver (Ag), is cemented optically to the hypotenuse of the prism 10 by optical immersion oil 12 or some other index-matchig material (e.g. epoxy). The sample under investigation 14 is placed on the conducting film, which for convenience is in a horizontal plane.

Figure 4:
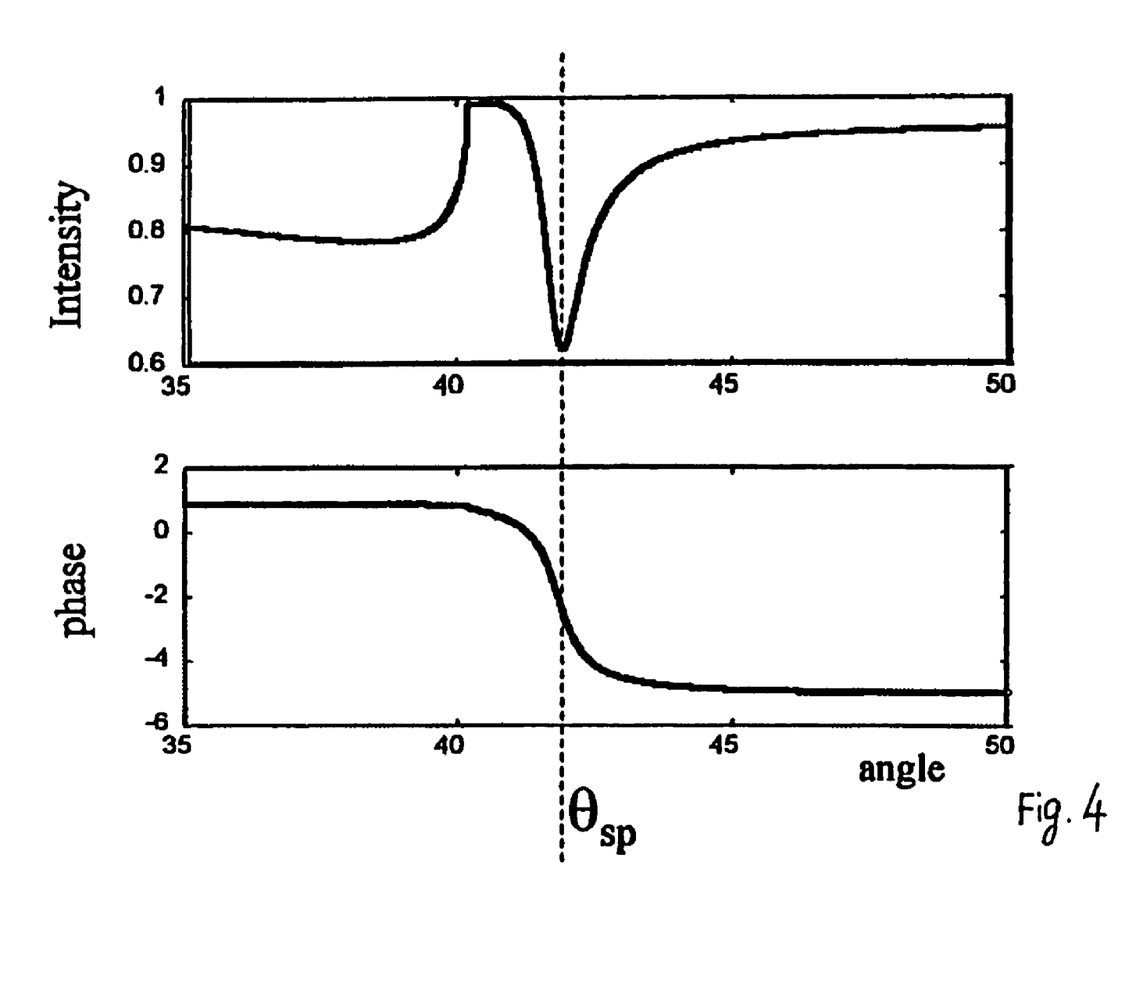
FIG. 4 shows graphically the relationship between the phase and intensity change of light on reflection from the sample to the angle of incidence, for a particular sample.

The light source 1 is a laser, preferably a He—Ne laser, whose light beam 15 is expanded, collimated and polarized in the p-polarization direction by a beam expander and collimator 2. In fact the light source may be a quasi monochromatic or polychromatic light source. The beam is incident on the sample slide through the one of the small faces of the prism 10, at the angle at which the plasma resonance is found to occur for the particular combination of sample and conducting film. (see FIG. 4 which shows graphically the relationship between the phase and intensity change of light on reflection from the sample to the angle of incidence, for a particular sample).

Before it reaches the prism 10, the incident light beam 15 passes through a beam-splitter 4, which takes out a small fraction of the beam to create the reference beam. With the aid of a mirror 6 and a second beam-splitter 7, this beam is recombined with the beam reflected from the sample so as to create an interference pattern. Such a system is known as a Mach-Zehnder interferometer.

With the aid of a lens 8, the plane of the sample is imaged onto a charge-coupled-device (CCD) camera 9, which is used to record the interferogram. It is noted that the image could alternatively be recorded on a permanent recording material such as photographic film using a conventional camera.

The output from the CCD camera 9 is put into a processing means—a computer, which first converts the image recorded by the CCD camera into a digital image. It then carries out an algorithm of the type discussed in ref. 1 in order to display the phase of the image at each pixel of the CCD recording. The data processing technique is based on a previous work by Kostianovsky et al. The basic idea consists of the use of Fourier's analysis in order to retrieve the phase change from a given interferogram. This technique has proved to be able to detect local changes in phase around $\pi/100$ radians between two given interferograms. For this procedure we need two interferograms: a reference $g_0(x,y)$ and a signal one $g(x,y)$.

Mathematically, the intensity of a reference interferogram can be written as:

$$g_0(x,y) = a(x,y) + b(x,y)\cos(\overline{\omega}_0 x + \phi_0(x,y))$$

$a(x,y)$, $b(x,y)$ and $\phi(x,y)$ represent local intensity variations and local phase variations as a result of intrinsic defects in the optical system. $\omega_0 = 2\pi\phi_0$ is the spatial frequency of the interferogram. Two strong spots at the main frequency characterize the Fourier transform of the reference picture.

When the phase is somehow changed by an external factor, the typical spatial frequency of the interferogram changes and it looks like:

$$g(x,y) = a(x,y) + b(x,y)\cos(\omega_0 x + \phi_0(x,y) + \phi(x,y))$$

The phase change is produced by a local modification of the refractive index in the dielectric sample deposited in the SPR unit. The frequency distortion arising around the main spots, caused by local changes in the sample.

The original captured and digitized pictures are "intensity pictures", so every pixel has a real value. The Fourier transform of a real picture is central-symmetric.

A proposed algorithm for the calculation of the phase change at each pixel can be as follows:

From the Fourier transformed pictures only the information centered on one of the two spots is taken and compared, the same one in both pictures. The spots G and $G_0$ can be written as:

$$G_0(u,v) = B(u,v) * P_0(u,v)$$

$$G(u,v) = B(u,v) * P_0(u,v) * P(u,v)$$

Where
$B(u,v) = FT\{b(x,y)\}$
$P_0(u,v) = FT\{\phi_0(x,y)\}$
$P(u,v) = FT\{\phi(x,y)\}$ From the inverse transform of G and $G_0$ the complex fields that represent the phase information of the interferogram are obtained. The pixel by pixel ratio between these two matrices is complex too. The phase of this new complex matrix is the local value of $\phi(x,y)$. The result is a map of phase changes between the reference and the object picture, for the entire field of view.

$$\phi(x,y) = phase\left\{\frac{FT^{-1}\{G(u,v)\}}{FT^{-1}\{G_0(u,v)\}}\right\}$$

This phase image is then converted to units of refractive index of the sample by using a known theoretical model for the plasma resonance mechanism (see for example Kabashin A. V. and Nikitin P. I., *Surface plasmon resonance interferomenter for bio-and chemical-sensorsor*. Opt. Commun. 150 (1998) 5–8) or by means of empirical calibration, which relates refractive index within the penetration layer to the phase of the reflected wave.

In the embodiment shown in FIG. 2, the light source is a He—Ne laser 1, whose ouput beam is expanded in diameter, collimated and polarized by the beam expander 2 and polarizer 3. The collimated and polarized beam is split into two beams which may be of unequal intensity by means of the beam-splitter 4, the stronger of the two beams continuing to the plasma resonance system 5, which is shown in more detail in FIG. 3. The weaker beam, reflected from beam-splitter 4, is further reflected from a mirror 6. After reflection from the system 5, which substantially weakens its intensity, the stronger beam is recombined with the weaker one by means of the beam-splitter 7. The combination of the two beams is them imaged by the lens 8 onto a CCD camera 9. The plasma resonance system 5, shown in FIG. 3, is constructed from a right-angled prism 10, onto which is placed a microscope slide 11, the space between them being filled with optical contacting oil 12. The side of the slide remote from the prism has deposited on it a thin layer 13 of silver (Ag) about 30 nm in thickness. The sample 14 under investigation is placed in close contact with this silver layer. The angle of incidence of the beam at the silver layer is $\theta_{sp}$ corresponding to the maximum gradient in the plot of reflection phase versus $\theta$ shown in FIG. 4 for that particular system. This plot is obtained from theoretical considerations, such as those described by Raether, and the angle $\theta_{sp}$ is typically 41°. The angle of the mirror 6 is changed until several interference fringes cross the field of view of the image. The image recorded by the CCD 9 is used as input to a computer with a frame-grabber, which digitizes the image. Using the analytical technique described by Kostianovsky et al., the desired image of plasma-resonance induced phase changes is obtained as output from the computer.

Figure 5:
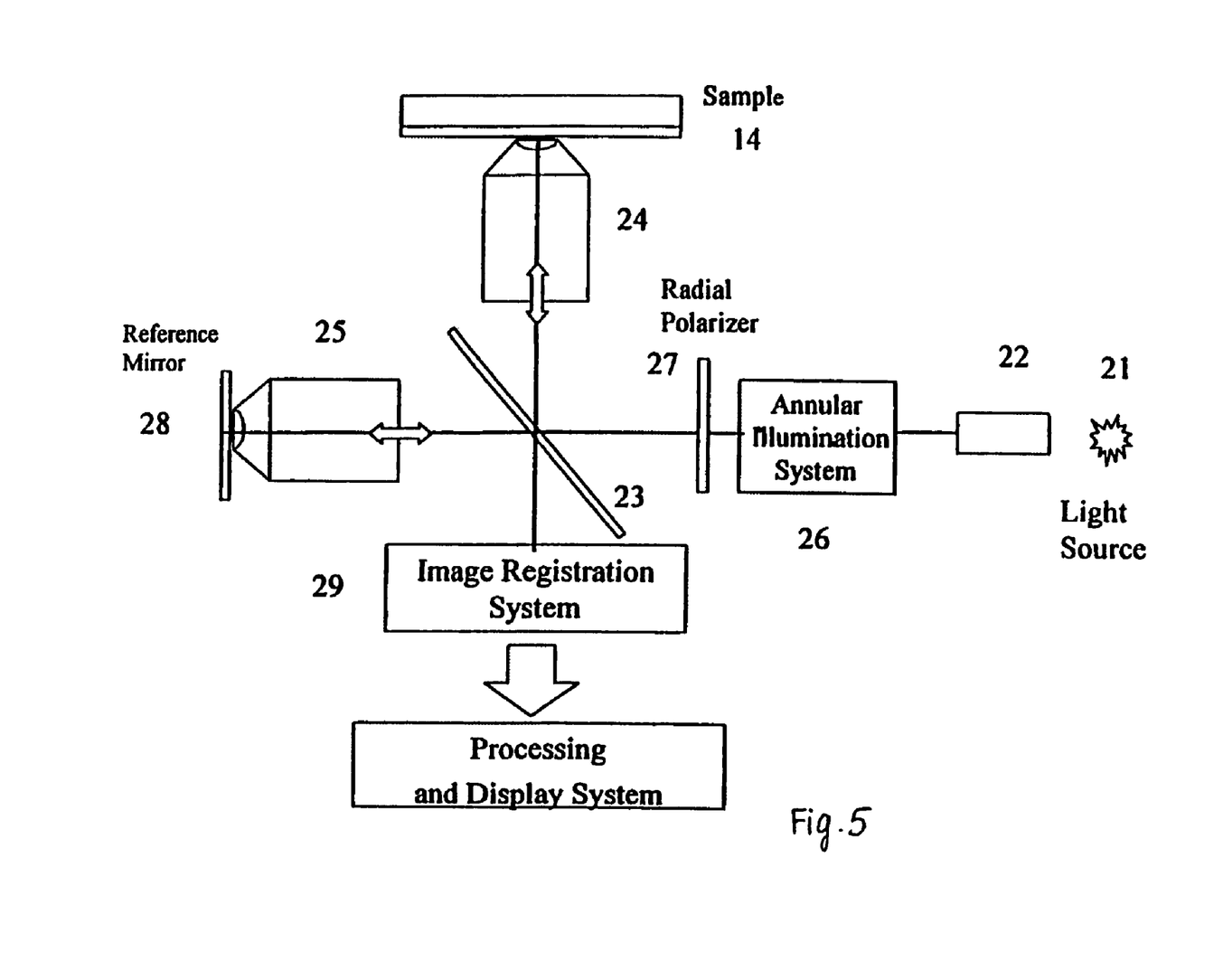
FIG. 5 shows a surface plasmon resonance imaging device in accordance with another preferred embodiment of the present invention, in which a Linnik interferometer is used, involving two microscope objectives, one of which is an immersion objective optically contacted with the reverse side of the slide on which the object is placed.
Figure 6:
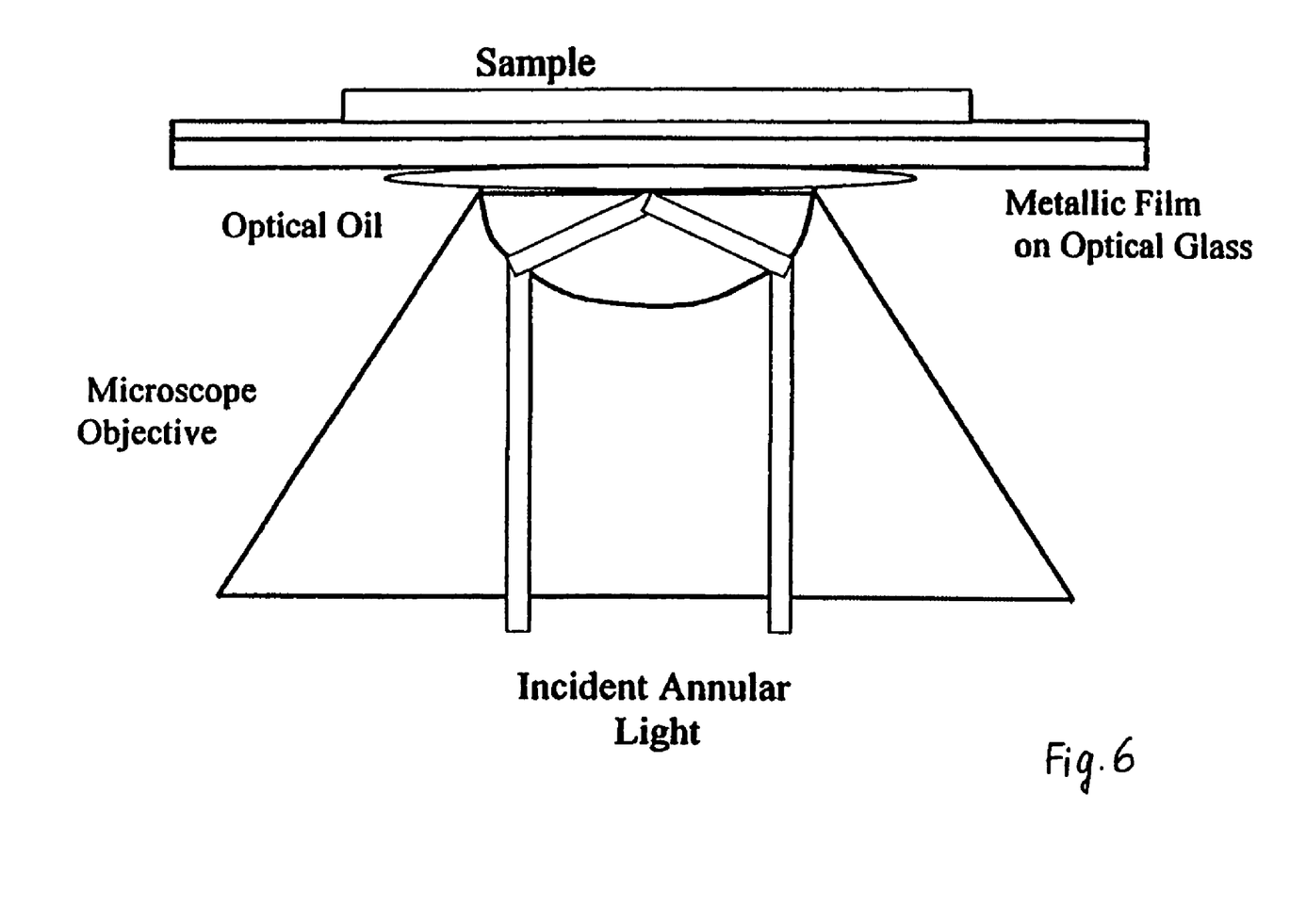
FIG. 6 shows in detail the construction and coupling of the sample and objective in the embodiment described in FIG. 5.

In a second embodiment of the invention, shown in FIG. 5, the interferometer used is a Linnik interferometer. The light source 21, which is also a laser, preferably a He—Ne laser, is expanded and collimated by a beam-expander 22 and is divided into two approximately equal parts by the beam-splitter 23. The right beam deflected and redirected at the sample is focussed onto the sample by means of an objective lens 24, and the light beam that is not deflected is focused onto a reference mirror 28 by means of a second substantially identical objective lens 25. The correct angle of incidence is selected by means of an annular illumination system 26 of variable radius focused into the focal plane of the objective lenses so as to illuminate the sample isotropically at an angle substantially equal to that at which the interaction with the plasma resonance is maximized. The illuminating beam is polarized radially by the radial polarizer 27. The reference mirror 28 has reflectivity that can be calculated and hence be predetermined to optimize the contrast of the interference pattern observed by the image registration system 29. The plasma resonance unit (30) applicable to this embodiment is a microscope slide 31 of suitable thickness onto which is deposited the thin film of conductor 32 (FIG. 6.). This slide 31 is attached optically to the lens 33 by immersion oil 34 in the conventional manner. The reference mirror 28 may also be a partially reflecting layer deposited on a microscope slide, which can be attached optically to its objective in the same way. However, the reference system, namely objective 25 and reference mirror 28 may be replaced by another optical system whose optical function is identical.

It should be clear that the description of the embodiments and the attached Figures set forth in this specification are provided for explanatory purposes only, without limiting the scope of the present invention as covered by the following claims.

It should also be clear that a person skilled in the art, after reading the present specification could make adjustments or amendments to the attached Figures and above described embodiments that would still be covered by the following claims.

What is claimed is:

1. A device for measuring simultaneously the phase at each point of an image formed by light reflected from a sample, in which the phase has been modified by plasma resonance in a thin conducting layer which is close to, or in contact with, the sample whose image is being recorded, the device comprising:
   a thick transparent substrate with a planar surface on which a thin layer of conducing material is deposited, onto which is placed the sample being investigated, either in contact with the thin layer of conducting material or a short distance from the layer;
   a light source linearly polarized in a predetermined direction, whose light beam is reflected from said thin layer of conducting material from the side opposite to that on which the sample is placed at an angle substantially equal to that at which the interaction with the plasma resonance is maximized, the evanescent light field on the far side of the conducting film interacting with the sample, thus modifying the reflected light;
   a Linnik interferometer which enables the reflected beam to be compared interferometrically with a reference beam derived from the same source, but not having had any interaction with the sample;
   an imaging means for recording an image of the planar surface in interference with the reference beam, and digitizing the recorded image; and
   a processing means for processing said digitized image to provide an output image, wherein the light beam is illuminated annularly, with appropriate radial polarization, so as to illuminate the sample isotropically at an angle substantially equal to that at which the interaction with the plasma resonance is maximized.

2. A device for measuring simultaneously the phase at each point of an image formed by light reflected from a sample, in which the phase has been modified by plasma resonance in a thin conducting layer which is close to, or in contact with, the sample whose image is being recorded, the device comprising:
   a thick transparent substrate with a planar surface on which a thin layer of conducting material is deposited, onto which is placed the sample being investigated, either in contact with the thin layer of conducting material or a short distance from the layer;
   a light source linearly polarized in a predetermined direction, whose light beam is reflected from said thin layer of conducting material from the side opposite to that at which the sample is placed at an angle substantially equal to that at which the interaction with the plasma resonance is maximized, the evanescent light field on the far side of the conducting film interacting with the sample, thus modifying the reflected light;
   an interferometer which enables the reflected beam to be compared interferometrically with a reference beam derived from the same source, but not having had any interaction with the sample;
   an imaging means for recording an image of the planar surface in interference with the reference beam, and digitizing the recorded image; and
   a processing means for processing said digitized image to provide an output image,
   wherein the light beam is illuminated annularly, with appropriate radial polarization, so as to illuminate the sample isotropically at an angle substantially equal to that at which the interaction with the plasma resonance is maximized.

* * * * *